United States Patent [19]

Nagubandi

[11] Patent Number: 4,457,873
[45] Date of Patent: Jul. 3, 1984

[54] PROCESS FOR PREPARING PHOSPHONOMETHYLATED AMINO ACIDS

[75] Inventor: Sreeramulu Nagubandi, Bedford Hills, N.Y.

[73] Assignee: Stauffer Chemical Company, Westport, Conn.

[21] Appl. No.: 478,192

[22] Filed: Mar. 24, 1983

[51] Int. Cl.$^3$ .............................. C07F 9/38
[52] U.S. Cl. .................. 260/502.5 F; 260/465.5 R; 260/926; 260/971; 560/145; 560/171
[58] Field of Search ............... 260/502.5 F, 465.5 R; 560/145, 171

[56] References Cited

U.S. PATENT DOCUMENTS

| | | | |
|---|---|---|---|
| 2,328,358 | 8/1943 | Pikl | 260/502.5 E |
| 3,160,632 | 12/1964 | Toy et al. | 260/502.5 F |
| 3,288,846 | 11/1966 | Irani et al. | 260/502.5 F |
| 3,799,758 | 3/1974 | Franz | 260/502.5 F |
| 3,956,370 | 5/1976 | Parry et al. | 260/502.5 F |
| 3,991,095 | 11/1976 | Gaertner | 71/87 |
| 4,035,177 | 7/1977 | Gaertner | 71/87 |
| 4,065,491 | 12/1977 | Pfliegel et al. | 260/502.5 F |
| 4,251,256 | 2/1981 | Kaufman | 260/502.5 F |

FOREIGN PATENT DOCUMENTS

| | | | |
|---|---|---|---|
| 55695 | 7/1982 | European Pat. Off. | 260/502.5 F |
| 1436844 | 6/1973 | United Kingdom | 260/502.5 F |

OTHER PUBLICATIONS

Franz, "Glyphosate and Related Chemistry", Adv. Pesticide Sci. Plenary Lect. Symp. Pap. Int. Congr. Pesticide Chem., 4th 1978 (pub. 1979), vol. 2, pp. 139–147.

*Primary Examiner*—J. E. Evans
*Attorney, Agent, or Firm*—Hensley M. Flash

[57] ABSTRACT

A process for preparing phosphonomethylated amino acids comprising phosphonomethylating a N-carboxymethyl-S-methylene bisdithiocarbamate with formaldehyde and a phosphorus source to obtain a phosphonomethylated bisdithiocarbamate which is then hydrolyzed to the phosphonomethylated amino acid salt. Acidification yields the corresponding phosphonomethylated amino acid, e.g. glyphosate, or acid derivative.

16 Claims, No Drawings

PROCESS FOR PREPARING PHOSPHONOMETHYLATED AMINO ACIDS

FIELD OF THE INVENTION

The present invention is a process for preparing phosphonomethylated amino acids and, in particular, for preparing N-phosphonomethylglycine, otherwise known as glyphosate.

BACKGROUND OF THE INVENTION

Certain phosphonomethylated amino acids, e.g. glyphosate and its derivatives, are herbicides. Herbicides are useful for controlling or modifying plant growth. Glyphosate and its derivatives are effective in controlling or modifying growth in a wide variety of plant species, including broadleaves, grasses and sedge.

Because glyphosate and its derivatives are so important, new processes for making it and its derivatives faster, cheaper or in greater yields are constantly in demand. A new process for preparing glyphosate from primary amino acids, esters or salts, e.g. glycine ethyl ester, has now been discovered.

When a primary amine is reacted with carbon disulfide and a base, a dithiocarbamic acid salt is formed. This salt can be reacted with dihalomethane to form methylene bisdithiocarbamate. The following reactions are typical:

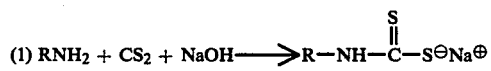

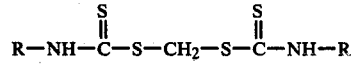

Such compounds have been used, for example, as fumigants and biocides.

BRIEF DESCRIPTION OF THE INVENTION

It has now been discovered that an N-carboxymethyl-S-methylene bisdithiocarbamate can be used to prepare phosphonomethylated amino acids such as glyphosate. Such acids can be obtained from an N-carboxymethyl-S-methylene bisdithiocarbamate by (1) phosphonomethylating at the nitrogen to obtain a phosphonomethylated bisdithiocarbamate; (2) hydrolyzing the phosphonomethylated bisdithiocarbamate to form a phosphonomethylated amino acid salt; and (3) acidifying the phosphonomethylated amino acid salt to obtain a phosphonomethylated amino acid or acid derivative.

The process is illustrated by the preparation of glyphosate or its derivatives, however other phosphonomethylated amino acids or their derivatives can be prepared by the process. In one preferred embodiment, the process comprises five steps. In the first step glycine or glycine ethyl ester or other amino acids, or salts or esters thereof are reacted with carbon disulfide and a base to form a salt. The salt is reacted with dihalomethane to form the N-carboxymethyl-S-methylene bisdithiocarbamate of the amino acid derivative used in the first step. The N-carboxymethyl-S-methylene bisdithiocarbamate is reacted with formaldehyde and a phosphorus source to form a phosphonomethylated bisdithiocarbamate. The phosphonomethylated bisdithiocarbamate is hydrolyzed and then acidified to give the phosphonomethylated amino acid or acid derivative. These reactions may be represented as follows:

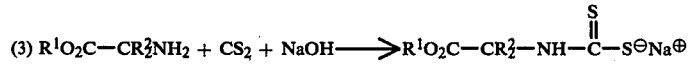

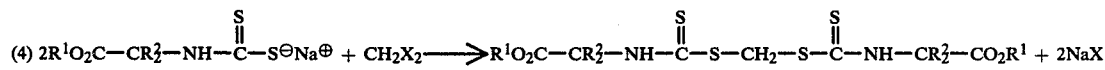

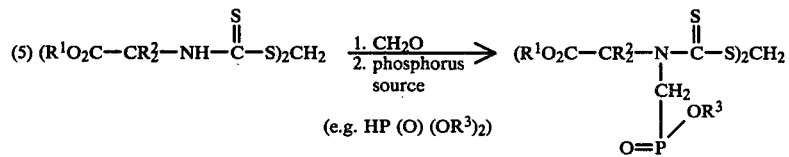

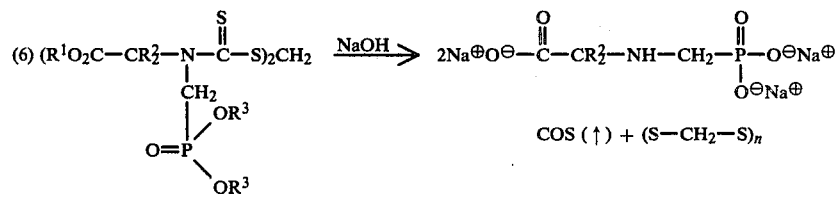

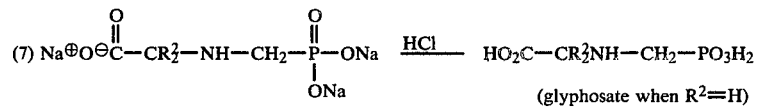

In reactions (3), (4), (5) and (6), $R^1$ is selected from the group consisting of an alkali metal; an alkaline earth metal; ammonium; an organic ammonium cation; hydrogen; alkyl having 1 to 8 carbon atoms, inclusive; and aryl, wherein aryl may be, for example, phenyl or substituted phenyl wherein the substituents may be alkyl having 1 to 4 carbon atoms, inclusive, alkoxy having 1 to 4 carbon atoms, inclusive and halogen.

In reactions (3), (4), (5), (6) and (7), $R^2$ is selected independently each time it occurs from the group consisting of hydrogen, a primary or secondary aliphatic alkyl having 1 to 8 carbon atoms, inclusive, alkenyl having 2 to 8 carbon atoms, inclusive and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive.

In reactions (5) and (6) $R^3$ is selected independently each time it occurs from the group consisting of hydrogen, alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen.

DETAILED DESCRIPTION OF THE INVENTION

In a step leading to this process, a N-carboxymethyl-S-methylene bisdithiocarbamate is prepared. A method of preparation includes reacting a primary amino acid or ester or salt or mixture thereof with carbon disulfide and a base to form a dithiocarbamate, then further reacting this dithiocarbamate with a dihalomethane. Other methods can be used to prepare this compound.

A N-carboxymethyl-S-methylene bisdithiocarbamate has the structure

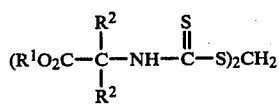

wherein $R^1$ is selected from the group consisting of an alkali metal; an alkaline earth metal; ammonium; an organic ammonium cation; hydrogen; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen. $R^2$ is selected independently each time it occurs from the group consisting of hydrogen, a primary or secondary aliphatic alkyl having 1 to 8 carbon atoms, inclusive, alkenyl having 2 to 8 carbon atoms, inclusive, and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive. In a preferred embodiment, $R^2$ is hydrogen and $R^1$ is either hydrogen, sodium, methyl or ethyl.

The base used to prepare the dithiocarbamate salt can be an organic base. Suitable bases include, but are not limited to, triethylamine, pyridine or an inorganic base such as sodium hydroxide or potassium hydroxide. In a preferred embodiment, the base used is sodium hydroxide or triethylamine.

The amino acid or ester or salt, carbon disulfide and base can be combined in a 1:1:1 mole ratio in the presence of a solvent. This 1:1:1 mole ratio is the stoichiometric ratio. Generally, up to about a 1:10 mole ratio of amino acid to carbon disulfide can be used with up to about a 1:3 mole ratio being desirable and up to about a 1:1.5 mole ratio being most preferable. Mole ratios above 1:10 of amino acid to carbon disulfide are not usually economical. For mole ratios of amino acid to base, generally up to about 1:3 can be used with up to about 1:2 being most preferable. The solvent can be, for example, water, or ethanol or other organic solvents such as toluene or tetrahydrofuran.

The reaction will proceed at temperatures in the general range of from about 0° C. to about 60° C. with temperatures from about 10° C. to about 30° C. being desirable and a temperature of about 20° C. being preferable. The dithiocarbamic acid salt is formed.

The dithiocarbamic acid salt is reacted with dihalomethane. The dihalomethane can be either dichloro- or dibromomethane.

The dithiocarbamic acid salt and the dihalomethane can be combined in a 1:0.5 mole ratio. This 1:0.5 mole ratio is the stoichiometric ratio. Generally, about a 0.5:10 mole ratio of the acid salt to the dihalomethane can be used with about a 0.5:2 mole ratio being desirable and about a 0.5:0.75 mole ratio being preferable. Mole ratios above 0.5:10 are usually not economical. The reaction proceeds with stirring to form N-carboxymethyl-S-methylene bisdithiocarbamate which can be, but need not be, isolated. This reaction will proceed at temperatures in the general range of from about 0° C. to about 60° C. with temperatures from about 10° C. to about 30° C. being desirable and a temperature of about 20° C. being preferable.

The N-carboxymethyl-S-methylene bisdithiocarbamate formed by the above procedure can then be phosphonomethylated in accordance with the processes of the present invention. The phosphonomethylation can be carried out by adding formaldehyde and a phosphorus source in the presence of a suitable acid or acid anhydride.

Suitable acids or anhydrides include, but are not limited to hydrochloric acid, acetic acid, and acetic anhydride. The formaldehyde may be used in the form of aqueous formaldehyde or solid paraformaldehyde. The mole ratio of N-carboxymethyl-S-methylene bisdithiocarbamate to formaldehyde can generally range up to about 1:10 with about a 1:5 mole ratio being desirable and about a 1:2.5 mole ratio being preferable. Mole ratios above 1:10 are usually not economical.

The formaldehyde may be added slowly to the N-carboxymethyl-S-methylene bisdithiocarbamate at temperatures generally ranging from about 5° C. to about 80° C. with a range of from about 5° C. to about 40° C. being desirable and a range of from about 5° C. to about 20° C. being preferable.

After the formaldehyde is added, the reaction mixture is stirred, preferably at least for an hour, at room temperature or at a temperature up to about 60–80° C.

The phosphorus source is of the formula

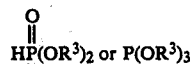

$$HP(OR^3)_2 \text{ or } P(OR^3)_3$$

wherein $R^3$ is selected independently each time it occurs from the group consisting of hydrogen, alkyl having 1 to 8 carbon atoms, inclusive; and aryl. Aryl may be, for example, phenyl or substituted phenyl wherein the substituents are alkyl having 1 to 4 carbon atoms, inclusive; alkoxy having 1 to 4 carbon atoms, inclusive; and halogen.

The mole ratio of N-carboxymethyl-S-methylene bisdithiocarbamate to phosphorus source can generally range up to about 1:10 with about a 1:5 mole ratio being desirable and about a 1:2.5 mole ratio being preferable. Mole ratios above 1:10 are usually not economical. The phosphorus source can be added to the flask containing the N-carboxymethyl-S-methylene bisdithiocarbamate and formaldehyde. The reaction mixture is heated to reflux, preferably for two to three hours.

The solvent is then removed from the phosphonomethylated bisdithiocarbamate by heating under vacuum or other means which are known for separating solvents from reaction mixtures. The phosphonomethylated bisdithiocarbamate is then hydrolyzed in the presence of a base.

To carry out the hydrolysis of phosphonomethylated bisdithiocarbamate, it is heated preferably to reflux temperature in the presence of a suitable strong base. Generally, a range of from about 4 moles to about 15 moles of base can be used with from about 4 moles to about 10 moles being desirable and about 4 moles to about 6 moles being preferable. Typically, at reflux temperatures, the reaction time ranges from about one hour to about ten hours with about one hour to about five hours being desirable and about one hour to about three hours being preferable. Suitable strong bases include, but are not limited to, sodium hydroxide and potassium hydroxide.

The reaction mixture is then acidified to about pH 4. Evaporation of the solvent yields a phosphonomethylated amino acid or acid derivative.

The following example shows a practical application of the process described. The final product obtained in this example is glyphosate.

EXAMPLE

Step 1: Synthesis of N-carboethoxymethyl-S-methylenebisdithiocarbamate:

Glycine ethyl ester hydrochloride (139.6 g, 1.0 mole) was dissolved in a mixture of ethanol (340 ml) and water (150 ml). To this solution, a solution of potassium hydroxide (112.2 g.) in water (20 ml) and carbon disulfide (120.6 ml) was simultaneously added. The reaction was exothermic. The reaction was stirred for 1 hr. and methylene bromide (42 ml) was added and the contents were heated to 50°–60° C. for 2 hrs. The solvent was evaporated and the residue was partitioned between water and chloroform. The chloroform was dried and evaporated to obtain N-carboethoxymethyl-S-methylene bisdithiocarbamate (M.P. 149°–152° C).

Step 2: Phosphonomethylation of N-carboethoxymethyl-S-methylene-bisdithiocarbamate:

To a solution of N-carboethoxymethyl-S-methylene bisdithiocarbamate (20.0 g, 0.054 mole) in glacial acetic acid (30 ml), paraformaldehyde (3.6 g, 0.119 mole) and phosphorus acid (9.8 g, 0.119 mole) was added. The reaction mixture was heated to reflux for 2 hrs. The small amount of solid that was present in the reaction mixture was filtered and the filtrate was evaporated to a yellowish oil. The product obtained was analyzed to be N-phosphonomethyl-N-carboxymethyl-S-methylene-bisdithiocarbamate.

Step 3. Hydrolysis of N-phosphonomethyl-N-carboxymethyl-S-methylene bisdithiocarbamate:

To a suspension of the above mentioned compound (4.0 g, 0.009 mole) in ethanol (100 ml), a solution of sodium hydroxide (1.8 g, 0.044 mole) in water (10 ml) was added. The reaction was exothermic and the reaction mixture was heated to 50° C. for 1 hr. More ethanol (15 ml) and water (15 ml) were added and the temperature was increased to 78°–80° C. for an additional 3 hrs. The reaction mixture was cooled and acidified to pH 4 and the solvent was removed under vacuum. The resulting crude mixture contained glyphosate along with sodium chloride. Sodium chloride was removed from the reaction mixture to obtain glyphosate.

What is claimed is:

1. A process for preparing a phosphonomethylated amino acid comprising:
    phosphonomethylating a N-carboxymethyl-S-methylene bisdithiocarbamate to obtain a phosphonomethylated bisdithiocarbamate; hydrolyzing said phosphonomethylated bisdithiocarbamate to form a phosphonomethylated amino acid salt; and
    acidifying said phosphonomethylated amino acid salt to obtain a phosphonomethylated amino acid or acid derivative.

2. A process as defined in claim 1 wherein said N-carboxymethyl-S-methylene bisdithiocarbamate has the structure

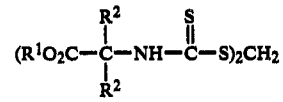

$$(R^1O_2C-\underset{R^2}{\underset{|}{C}}-NH-\overset{S}{\overset{\|}{C}}-S)_2CH_2$$

wherein $R^1$ is selected from the group consisting of an alkali metal; an alkaline earth metal; ammonium; an organic ammonium cation; hydrogen; alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen; and $R^2$ is selected independently each time it occurs from the group consisting of hydrogen, a primary or secondary aliphatic alkyl having 1 to 8 carbon atoms, inclusive, alkenyl having 2 to 8 carbon atoms, inclusive, and alkynyl having 2 to 8 carbon atoms, inclusive, wherein said alkyl, alkenyl or alkynyl are optionally substituted with a member of the group consisting of halogen; a hydroxy group; an amine; a cyano group; a carboxy group; alkoxy having 1 to 4 carbon atoms, inclusive; an amido group; a thio group; a sulfide group having 1 to 4 carbon atoms, inclusive; aryloxy having 6 to 12 carbon atoms, inclusive; alkoxy carbonyl having 1 to 8 carbon atoms, inclusive; phenyl; aryl having 6 to 12 carbon atoms, inclusive; carboxyaryl having 7 to 12 carbon atoms, inclusive; amino alkyl amine having 1 to 8 carbon atoms, inclusive; alkoxyalkoxy having 2 to 8 carbon atoms, inclusive; and a heterocyclic group having 2 to 12 carbon atoms, inclusive.

3. A process as defined in claim 2 wherein $R^1$ is hydrogen.

4. A process as defined in claim 2 wherein $R^1$ is methyl.

5. A process as defined in claim 2 wherein $R^1$ is ethyl.

6. A process as defined in claim 2 wherein $R^2$ is hydrogen.

7. A process as defined in claim 1 wherein the N-carboxymethyl-S-methylene bisdithiocarbamate is obtained by reacting a primary amino acid, ester or salt with carbon disulfide and a base to form a dithiocarbamate then further reacting said dithiocarbamate with dihalomethane.

8. A process as defined in claim 7 wherein the dihalomethane is dichloromethane.

9. A process as defined in claim 7 wherein the dihalomethane is dibromomethane.

10. A process as defined in claim 1 wherein said N-carboxymethyl-S-methylene bisdithiocarbamate is phosphonomethylated using formaldehyde and a phosphorus source.

11. A process as defined in claim 10 wherein said formaldehyde is used in the form of aqueous formaldehyde.

12. A process as defined in claim 10 wherein said formaldehyde is used in the form of paraformaldehyde.

13. A process as defined in claim 10 wherein said phosphorus source has the structure

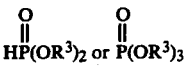

wherein $R^3$ is selected independently each time it occurs from the group consisting of hydrogen, alkyl having 1 to 8 carbon atoms, inclusive; phenyl and substituted phenyl wherein the substituents are selected from the group consisting of alkyl having 1 to 4 carbon atoms, inclusive; alkoxy having 1 to 4 carbon atoms, inclusive; and halogen.

14. A process as defined in claim 13 wherein said N-carboxymethyl-S-methylene bisdithiocarbamate is phosphonomethylated by:
adding at least 2 mole equivalent of formaldehyde slowly to said N-carboxymethyl-S-methylene bisdithiocarbamate at room temperature to form a reaction mixture; and
subsequently adding at least 2 mole equivalent of said phosphorus source to said reaction mixture to obtain a phosphonomethylated bisdithiocarbamate.

15. A process as defined in claim 14 wherein said phosphonomethylated bisdithiocarbamate is heated to refux.

16. A process for preparing glyphosate comprising:
reacting glycine with carbon disulfide and a base to form a salt;
further reacting said salt with dihalomethane to form N-carboxymethyl-S-methylene bisdithiocarbamate;
phosphonomethylating said N-carboxymethyl-S-methylene bisdithiocarbamate to obtain a phosphonomethylated bisdithiocarbamate;
hydrolyzing said phosphonomethylated bisdithiocarbamate to form a phosphonomethylated glycine salt; and
acidifying said phosphonomethylated glycine salt to obtain glyphosate.

* * * * *